(12) United States Patent
Stevens et al.

(10) Patent No.: US 8,684,964 B2
(45) Date of Patent: Apr. 1, 2014

(54) INFLATION SENSOR MOUNT AND METHOD OF ASSEMBLY

(75) Inventors: Brian Stevens, Pleasant Grove, UT (US); Blaine Johnson, Riverton, UT (US); Randy Boyd, Riverton, UT (US); Steve Taylor, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 13/523,611

(22) Filed: Jun. 14, 2012

(65) Prior Publication Data

US 2013/0338581 A1     Dec. 19, 2013

(51) Int. Cl.
*A61M 29/00*     (2006.01)

(52) U.S. Cl.
USPC ................................................. 604/99.01

(58) Field of Classification Search
USPC ................................................. 604/99.01
See application file for complete search history.

(56) References Cited

U.S. PATENT DOCUMENTS

| 4,195,637 | A | 4/1980 | Gruntzig et al. |
| 4,370,982 | A | 2/1983 | Reilly |
| D274,470 | S | 6/1984 | Lundquist |
| 4,655,749 | A | 4/1987 | Fischione |
| 4,743,230 | A | 5/1988 | Nordquest |
| 4,841,977 | A | 6/1989 | Griffith et al. |
| 5,084,060 | A | 1/1992 | Freund et al. |
| 5,135,488 | A | 8/1992 | Foote et al. |
| 5,201,753 | A | 4/1993 | Lampropoulos et al. |
| 5,259,838 | A | 11/1993 | Taylor et al. |
| 5,284,480 | A | 2/1994 | Porter et al. |
| 5,300,027 | A | 4/1994 | Foote et al. |
| 5,385,549 | A | 1/1995 | Lampropoulos et al. |
| 5,425,713 | A | 6/1995 | Taylor et al. |
| 5,431,629 | A | 7/1995 | Lampropoulos et al. |
| 5,449,344 | A | 9/1995 | Taylor et al. |
| 5,449,345 | A | 9/1995 | Taylor et al. |
| 5,453,091 | A | 9/1995 | Taylor et al. |
| 5,562,621 | A | 10/1996 | Claude et al. |
| 5,599,301 | A | 2/1997 | Jacobs et al. |
| 5,741,229 | A | 4/1998 | Robinson et al. |
| 5,749,853 | A | 5/1998 | O'Donnell et al. |
| 6,190,354 | B1 | 2/2001 | Sell et al. |
| 6,234,996 | B1 | 5/2001 | Bagaoisan et al. |
| 6,394,977 | B1 * | 5/2002 | Taylor et al. ............. 604/100.03 |

(Continued)

FOREIGN PATENT DOCUMENTS

| EP | 0199083 | 4/2002 |
| WO | WO92/17221 | 10/1992 |
| WO | WO 2009/137225 | 11/2009 |
| WO | WO 2010/075083 | 7/2010 |

OTHER PUBLICATIONS

Notice of Allowance dated Jan. 9, 2013 for U.S. Appl. No. 13/399,712.

(Continued)

*Primary Examiner* — Jason Flick
(74) *Attorney, Agent, or Firm* — Stoel Rives LLP

(57) ABSTRACT

An inflation device comprising a housing configured to receive a sensor assembly is disclosed. In some embodiments, the sensor assembly may be coupled to the housing through use of a snap fit-type connection. Further, the working fluid of the inflation device may be in direct communication with the pressure sensor, without the use of secondary fluids such as gels.

18 Claims, 8 Drawing Sheets

(56) References Cited

U.S. PATENT DOCUMENTS

| | | |
|---|---|---|
| 6,533,757 B1 | 3/2003 | Lampropoulos et al. |
| 7,051,594 B1 | 5/2006 | Aziz |
| D597,037 S | 7/2009 | Lampropoulos et al. |
| 7,892,202 B2 | 2/2011 | Lampropoulos et al. |
| 8,118,776 B2 | 2/2012 | Lampropoulos et al. |
| 8,398,588 B1 | 3/2013 | Lampropoulos et al. |
| 2002/0045854 A1 | 4/2002 | Royo et al. |
| 2004/0193045 A1 | 9/2004 | Nelson et al. |
| 2008/0097294 A1 | 4/2008 | Prather et al. |
| 2009/0281489 A1 | 11/2009 | Lampropoulos et al. |

OTHER PUBLICATIONS

International search report and Publication for PCT/US2009/040310 (WO2009/137225) dated Nov. 12, 2009.

Office action dated Dec. 10, 2009 in U.S. Appl. No. 12/118,442.

Office Action dated Jul. 8, 2010 in U.S. Appl. No. 12/118,442.

Notice of Allowance and Fees Due dated Oct. 7, 2011 in U.S. Appl. No. 12/638,631.

Notice of Allowance and Fees Due dated Oct. 28, 2010 in U.S. Appl. No. 12/118,442.

European Search Report dated Oct. 17, 2011 for PCT/US2009/040310.

Restriction Requirement dated Jan. 24, 2011 for U.S. Appl. No. 12/638,631.

Office Action dated Mar. 23, 2011 for U.S. Appl. No. 12/638,631.

Notice of Allowance dated Aug. 18, 2011 for U.S. Appl. No. 12/638,631.

International Search Report and Written Opinion dated Sep. 2, 2013 for PCT/US2013/045600.

\* cited by examiner

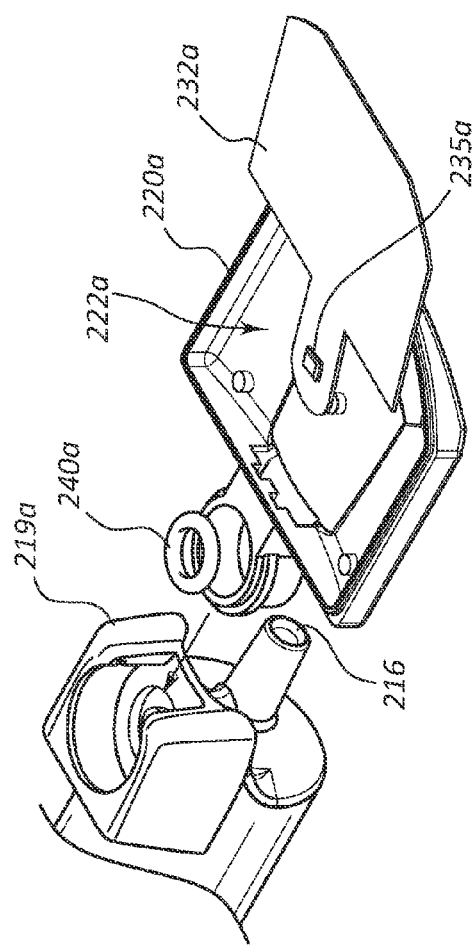
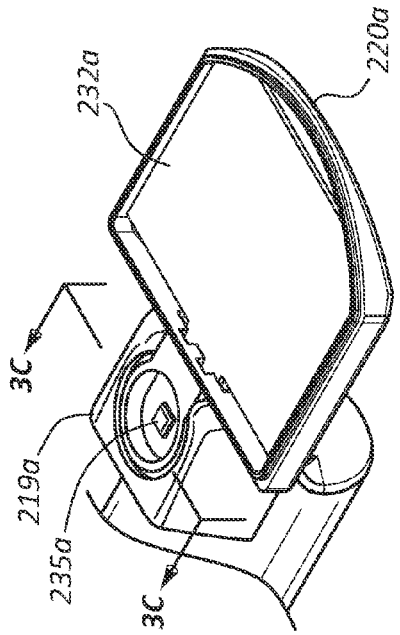
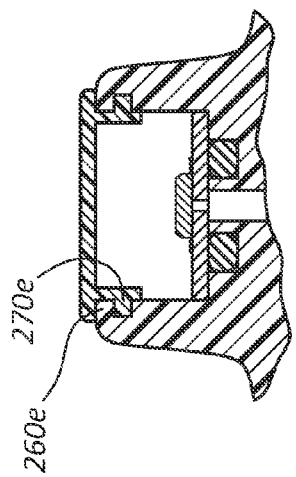
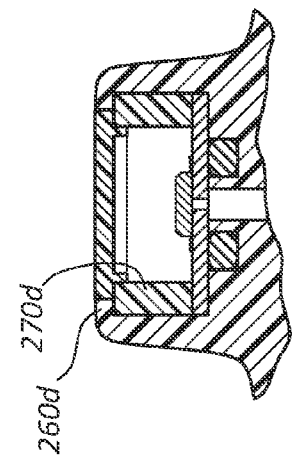
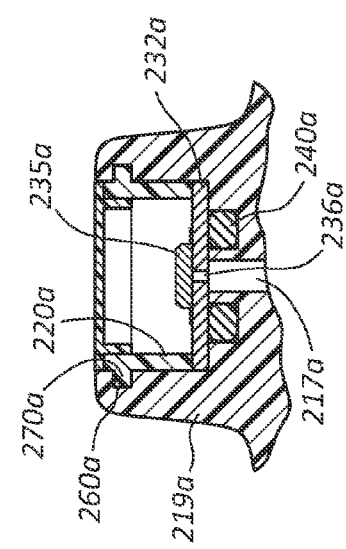
FIG. 3A
FIG. 3B
FIG. 3C
FIG. 3D
FIG. 3E

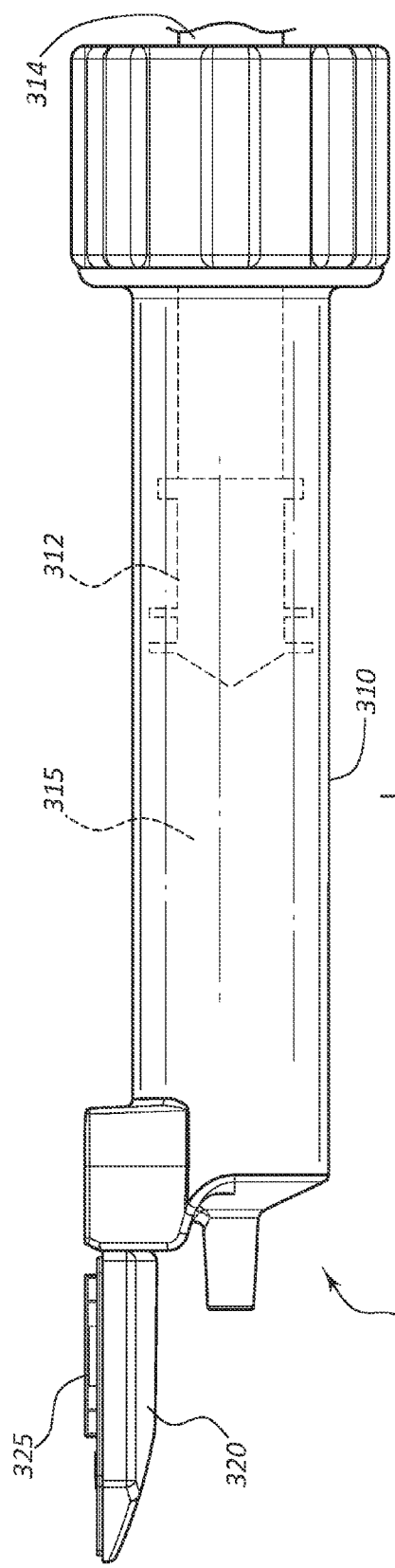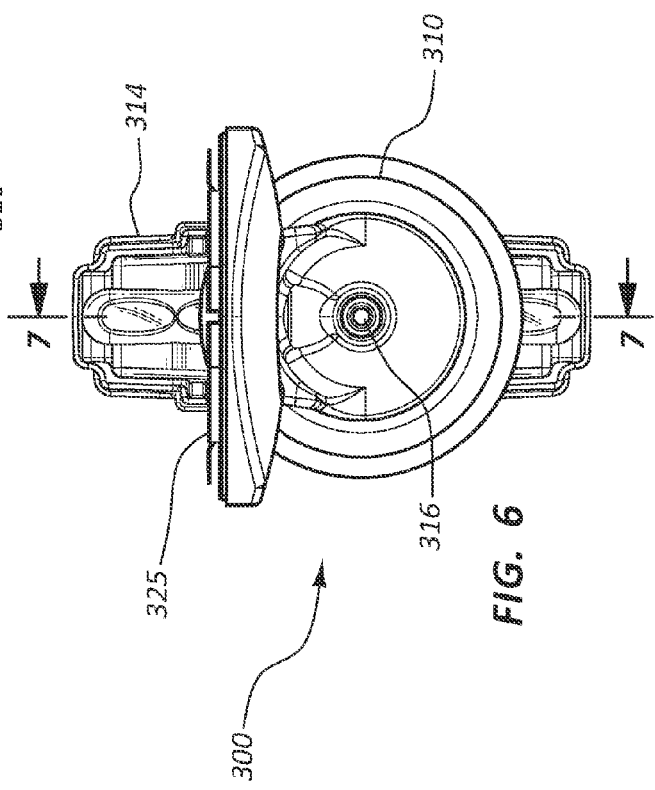

INFLATION SENSOR MOUNT AND METHOD OF ASSEMBLY

TECHNICAL FIELD

The present disclosure relates generally to devices used to pressurize, depressurize, or otherwise displace fluid, particularly in medical devices. More specifically, the present disclosure relates to inflation devices that may comprise pressure sensors coupled to the inflation device.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 5 is a side view of an inflation device and housing.

FIG. 6 is an end view of the inflation device and housing of FIG. 5.

DETAILED DESCRIPTION

Figure 1:
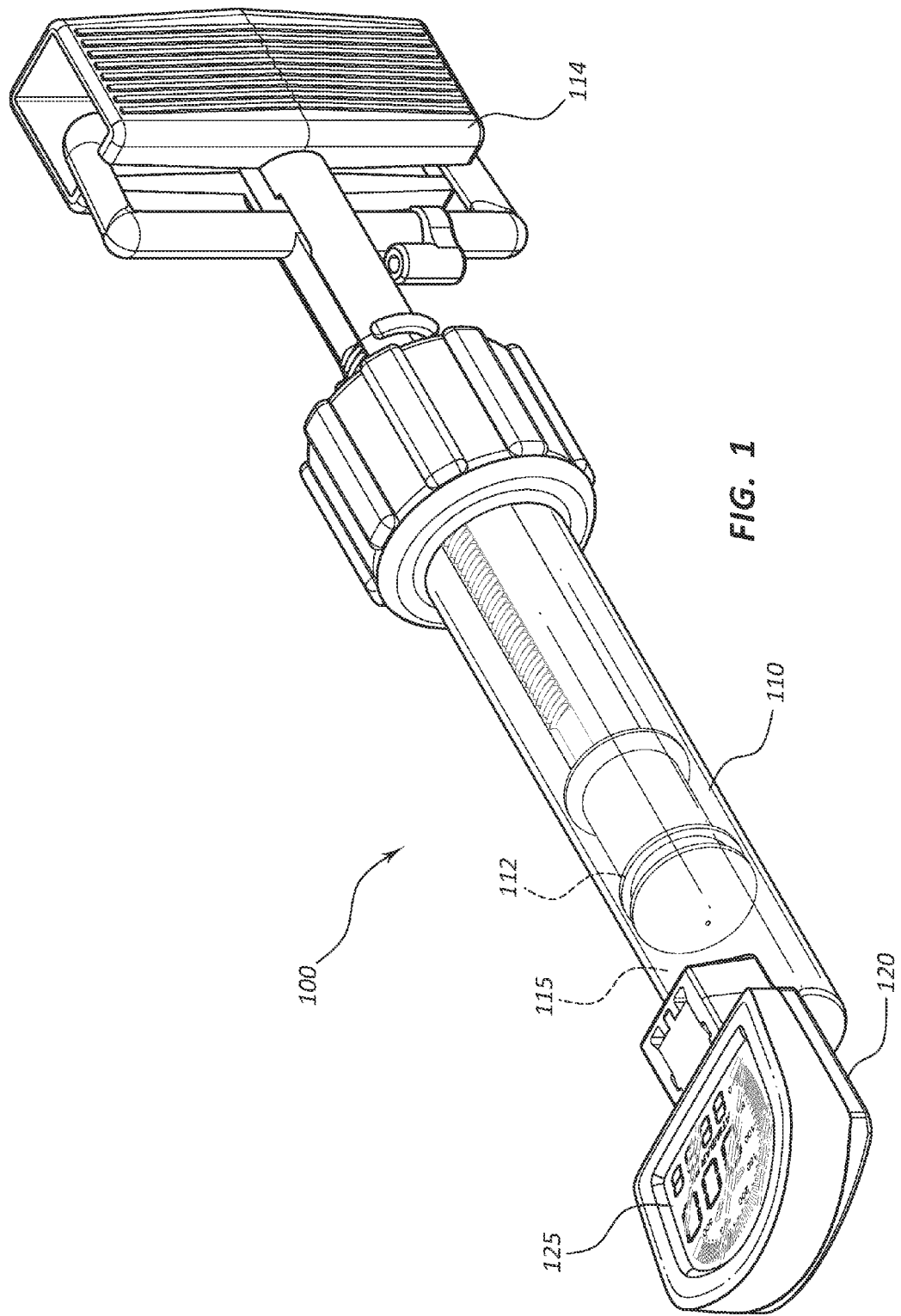
FIG. 1 is a top perspective view of an inflation device.

An inflation device may be configured for use in connection with a variety of medical procedures. For example, inflation devices may be used in connection with balloons or other medical devices in a variety of therapies, such as angioplasty, stent expansion, valvuloplasty, and so on. In some embodiments, a pressure sensor may be used in connection with an inflation device to determine the pressure inside the inflation device and attached components, such as balloons. As further detailed below, a sensor assembly may be coupled to an inflation device through a snap fit-type connection.

Snap fit designs may obviate the need to couple the sensor assembly and inflation device with adhesive or other fasteners. This may, in turn, reduce the incidence of failure or leakage of the fasteners. Further, in some instances, the pressure sensor may be in direct fluid communication with the working fluid within the inflation device, without the use of gels or other fluids to transfer pressure from the working fluid of the inflation device to the pressure sensor.

It will be readily understood by one of ordinary skill in the art having the benefit of this disclosure, that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the body portion of an inflation device, the proximal end of the body refers to the end nearest the handle and the distal end refers to the opposite end, the end nearest the inlet/outlet port of the inflation device. Thus, if at one or more points in a procedure a physician changes the orientation of an inflation device, as used herein, the term "proximal end" always refers to the handle end of the inflation device (even if the distal end is temporarily closer to the physician).

"Fluid" is used in its broadest sense to refer to any fluid, including both liquids and gasses as well as solutions, suspensions, etc., which generally behave as a fluid. "Fluid communication" refers to the ability of fluids to travel or transfer pressure from one position to another, without substantial impediment. Thus, two areas may be in fluid communication if fluids in those areas are able to interact. A particular area may be isolated from fluid communication with another area in some instances. In other words, fluids within two isolated areas cannot substantially interact. Fluids in a particular portion of a device may be isolated from the environment, meaning there is no substantial direct fluid interaction between fluids within that area and ambient fluids.

FIG. 1 is a top perspective view of an inflation device 100. In the illustrated embodiment, a body portion 110 is shown in connection with a plunger 112 and a handle 114. The inflation device body portion 110 further comprises a fluid chamber, referred to as an interior portion 115. The plunger 112 may be axially displaceable within the interior portion 115 such that displacement of the plunger 112 may be configured to displace fluid within the interior portion 115. For example, displacement of the plunger 112 in a distal direction may increase pressure within the interior portion 115 and/or force fluid from an outlet (116 of FIG. 2) of the inflation device 100. In some embodiments a medical device, such as a balloon, may be coupled to, and in fluid communication with, the outlet (116 of FIG. 2), such that increasing the pressure within the interior portion 115 also increases pressure within the medical device.

The embodiment of FIG. 1 further comprises a housing 120 coupled to the body portion 110. The housing 120 may be configured to couple a pressure sensor (not shown) to the housing 120. The pressure sensor may be configured to read the pressure within the interior portion 115 and display the pressure on a display component 125. The display component 125 may be analog or digital and may displace numeric and/or non-numeric indicia of the pressure.

Figure 2:
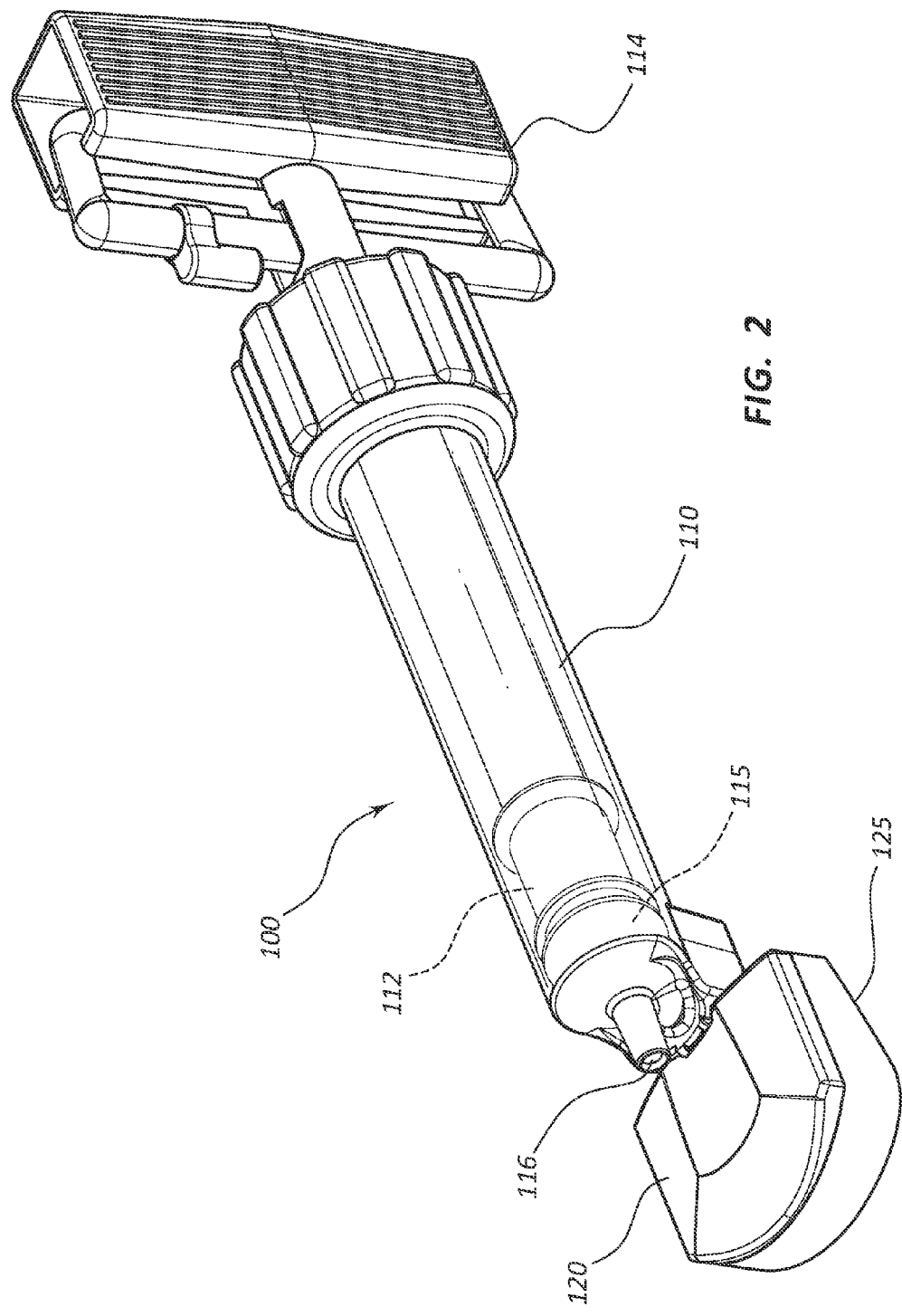
FIG. 2 is a bottom perspective view of the inflation device of FIG. 1.

FIG. 2 is a bottom perspective view of the inflation device 100 of FIG. 1. The housing 120 may be integrally formed with the body portion 110 of the inflation device 100, or it may be formed of a separate component and coupled to the body portion 110. The housing 120 may be positioned such that it creates minimal interference with the outlet 116 while also configured to orient the display 125 toward a user. FIG. 2 further illustrates the handle 114 of the inflation device 100 as well as the interior portion 115 and plunger 112.

Figure 3:
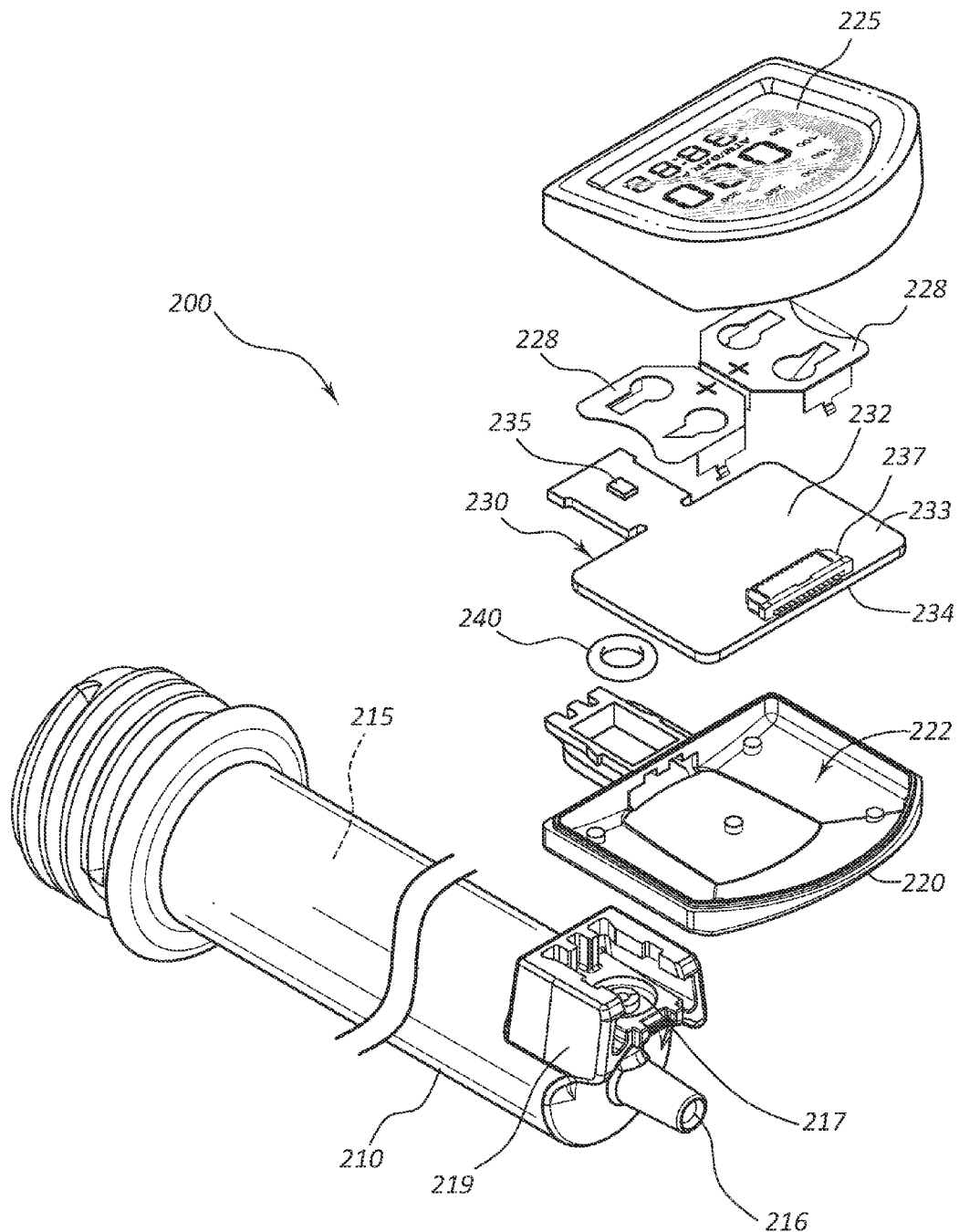
FIG. 3 is an exploded top view of a sensor assembly for use in connection with an inflation device.
Figure 3F:
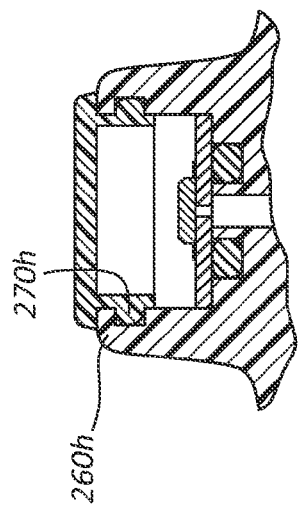
FIGS. 3D-3I are cross sectional views of exemplary embodiments of snap fit connections.
Figure 3G:
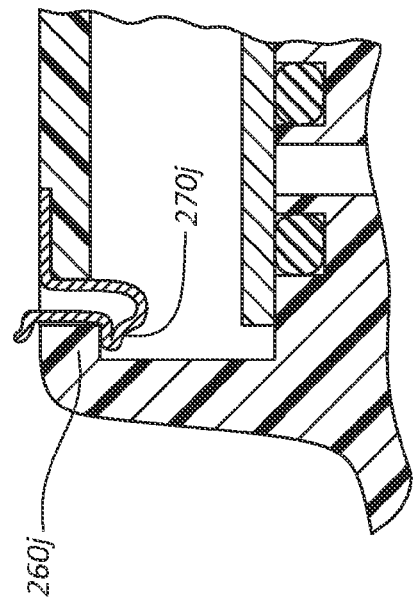
Figure 3H:
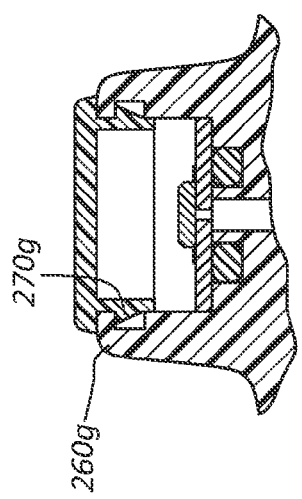
Figure 3K:
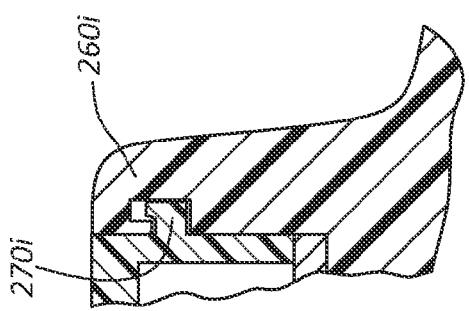
FIG. 3A is a partial perspective view of a circuit board and housing in a first configuration.
FIG. 3B is a partial perspective view of the circuit board and housing of FIG. 3A in a second configuration.
FIG. 3C is a cross sectional view of a portion of the circuit board and housing of FIG. 3B, taken through plane 3C-3C.

FIG. 3 is an exploded top view of a sensor assembly 230 and mounting components configured for use in connection with an inflation device 200. The inflation device 200 of FIG. 3 can, in certain respects, resemble components of the inflation device 100 described in connection with FIGS. 1-2 above. It will be appreciated that all the illustrated embodiments may have analogous features. Accordingly, like features are designated with like reference numerals, with the leading digits incremented to "2." (For instance, the inflation device is designated "100" in FIG. 1, and an analogous inflation device is designated as "200" in FIG. 3.) Relevant disclosure set forth above regarding similarly identified features thus may not be repeated hereafter. Moreover, specific features of the inflation device and related components shown in FIG. 3 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the inflation device of FIG. 3. Any suitable combination of the features, and variations of the same, described with respect to the inflation device and components illustrated in FIGS. 1-2, can be employed with the inflation device and components of FIG. 3, and vice versa. This pattern of disclosure applies equally to further embodiments depicted in subsequent figures and described hereafter.

The inflation device 200 of FIG. 3 comprises a body portion 210 having an interior portion 215 in fluid communication with an outlet 216. The inflation device 200 further comprises a housing 220 configured to be coupled to a housing mount 219 that is integrally formed with the body portion 210. The housing 220 may be coupled to the housing mount 219 in a variety of ways, including the use of fasteners, adhesive, snap fit connections, and so forth. As also described above, in other embodiments, the housing 220 may be integrally formed with the body portion 210. A display 225 and a battery holder 228 are also illustrated in connection with the housing 219 and sensor assembly 230.

The inflation device 200 of FIG. 3 further comprises a sensor assembly 230. The sensor assembly 230 comprises a circuit board 232 having a first surface (top surface 233) and a second surface (bottom surface 234). The sensor assembly 230 may further comprise one or more connection points 237 configured to connect components of the sensor assembly 230 with other components of the inflation device 200, such as the battery holder 228 and/or the display 225. Furthermore, in some embodiments, the display 225 may be coupled directly to the circuit board 232.

The housing 220 may comprise an interior sensor assembly receiving portion 222, configured to receive the circuit board 232 and other components of the sensor assembly 230. In some embodiments, the circuit board 232 may be configured as just smaller than the sensor assembly receiving portion 222, allowing the circuit board 232 to fit within the sensor assembly receiving portion 222.

The circuit board 232 and other components of the sensor assembly 230 may be configured to be coupled to the housing 220. In some embodiments, the sensor assembly 230 may couple to the housing 220 through a snap fit connection. As used herein, snap fit-type connections refer very broadly to a wide variety of fits or connections, such as connections which rely on friction between component parts (as opposed to adhesive or mechanical fasteners) to couple the component parts. In some embodiments, snap fit connections may comprise a groove or slot in a first component, configured to receive a second component. One or more protrusions, tabs, ridges, ribs, barbs, or other locking feature may be disposed such that the feature is deformed when the second component is pushed into the receiving portion of the second component. Once the second component is in place, the locking feature may return to its initial position and lock the second component in place.

Referring to FIG. 3, for example, the sensor assembly receiving portion 222 may include a groove configured to mate with the outside edge of the circuit board 232. The rest of the sensor assembly receiving portion 222 may be just smaller than the circuit board 232, requiring the housing 220, the circuit board 232, or both to slightly deform into order to push the circuit board 232 into the groove. Once the circuit board 232 is in the groove, contact and friction between the circuit board 232 and the housing 220 will constrain the movement of the circuit board 232 with respect to the housing 220.

FIGS. 3A and 3B illustrate one embodiment of a circuit board 232a being disposed within a receiving portion 222a of a housing 220a for coupling to a housing mount 219a. A pressure sensor 235a may be coupled directly to the circuit board 232a. An o-ring 240a is also shown in connection with this assembly. Each component of this assembly may be configured to be coupled together through use of one or more snap fit connections. FIG. 3C is a cross sectional view of a portion of the circuit board 232a and housing 220a of FIGS. 3A and 3B, taken through plane 3C-3C. As shown in FIG. 3C, the circuit board 232a may be configured to exert pressure on the o-ring 240a when the components are assembled. In some embodiments, this pressure may result from positional constraints on the circuit board 232a by the snap fit connection. FIG. 3C also illustrates how an aperture 217a and circuit board aperture 236a may provide fluid communication with the sensor 235a when the device is assembled.

In the embodiment illustrated in FIG. 3C, some elements of a snap fit connection between the housing mount 219a and the housing 220a are illustrated. Specifically, the snap fit connection comprises a first portion 260a configured to work cooperatively with a second portion 270a to constrain the two portions with respect to each other. In this embodiment, one or both portions 260a, 270a may deform slightly when the portions are snapped together. In some embodiments, the circuit board 232a may also or alternatively be configured with a snap fit type connection to an adjacent element, such as the housing 220a. For instance, in some embodiments, the housing 220a may be integrally formed with the housing mount 219a, and the circuit board 232a snap fits into the housing 220a. In other embodiments, additional components may have snap fit connections, including embodiments wherein one or more components comprising snap fit portions are also configured to interact with—and constrain—other components which may not have a snap fit portion. For example, the o-ring 240a may be constrained by pressure from elements having snap fit portions, though the o-ring may not directly have such a portion.

A wide variety of features (e.g., protrusions, tabs, ridges, barbs, slots, channels, holes, and so on) may be configured for use in connection with a snap fit. In embodiments wherein the sensor assembly 230 is configured to snap fit into the housing 220, mating features may be found on both components, or features may only be identifiable on one of the two components. Still further, in some embodiments protruding-type locking elements (e.g., barbs, ridges, and so on) may be on either or both components and receiving-type locking elements (e.g., grooves, slots, and so on) may be on either or both components. For example in FIG. 3C, a groove or receiving portion of the first snap fit portion 260a is configured to receive a square protrusion of the second snap fit portion 270a.

FIGS. 3D-3I illustrate additional potential components and shapes of snap fit systems. In each embodiment, a first snap fit portion is indicated by reference numeral 260x and second snap fit portion by numeral 270x, with x corresponding to the letter associated with each figure. As shown, the protruding-type elements and the receiving-type elements may have a variety of shapes, sizes, and configurations. The illustrated components are illustrative only and not meant to be exhaustive. Again, any snap fit element shown may be fixed to either of the two components to couple them together.

As shown in FIG. 3, the sensor assembly 230 may further comprise a pressure sensor 235. In the illustrated embodiment, the pressure sensor 235 is coupled to the top surface 233 of the circuit board 232. The pressure sensor 235 may be configured such that only one side of the pressure sensor 235 detects pressure. In some embodiments—such as that of FIG. 3—the pressure sensing side of the pressure sensor 235 may be disposed adjacent the bottom surface 234 of the circuit board 232. In other embodiments, the pressure sensor 235 may be coupled to the bottom surface 234 of the circuit board 232. In either case, and as further described herein, the pressure sensor 235 may be configured to be in direct fluid communication with the interior portion 215 of the body portion 210. Thus, in some embodiments, no secondary fluid—such as a gel—is disposed between the pressure sensor 235 and the interior portion 215. A system configured for use without a gel or secondary fluid may remove the risk that inconsistencies (such as bubbles or leaks) in the secondary fluid will undesirably alter sensor measurements.

In the embodiment of FIG. 3, an aperture 217 extends between the interior portion 215 and the housing mount 219. When assembled, the components of the inflation device 200 may be configured such that the aperture 217 provides fluid communication between the interior portion 215 and a sensing portion of the sensor assembly 230. In embodiments wherein the pressure sensor 235 is coupled to the bottom surface 234 of the circuit board 232, the pressure sensor 235 may simply be disposed adjacent the aperture 217. In embodiments wherein the pressure sensor 235 is coupled to the top surface 233 of the circuit board 232, a circuit board aperture (not shown) may provide fluid communication between the aperture 217 and the pressure sensor 235.

A seal, such as o-ring 240, may be configured to isolate the pressure sensor 235 from the outside environment. In other words, the seal may be positioned such that the pressure sensor 235 is in fluid communication with the interior portion 215 but not with other areas of pressure. In the illustrated embodiment, the o-ring 240 is configured to be disposed around the aperture 217 such that the o-ring 240 seals the fluid communication between the pressure sensor 235 and the aperture 217 when the inflation device 200 is assembled. In some embodiments the circuit board 232 and housing 220 may be configured to exert compressive forces on the o-ring 240 when the circuit board 235 and housing 220 are coupled. In some instances the receiving portion of a snap fit design may be positioned such that the circuit board 235 and/or housing 220 must partially compress the o-ring 240 in order to be snapped into place.

Figure 4:
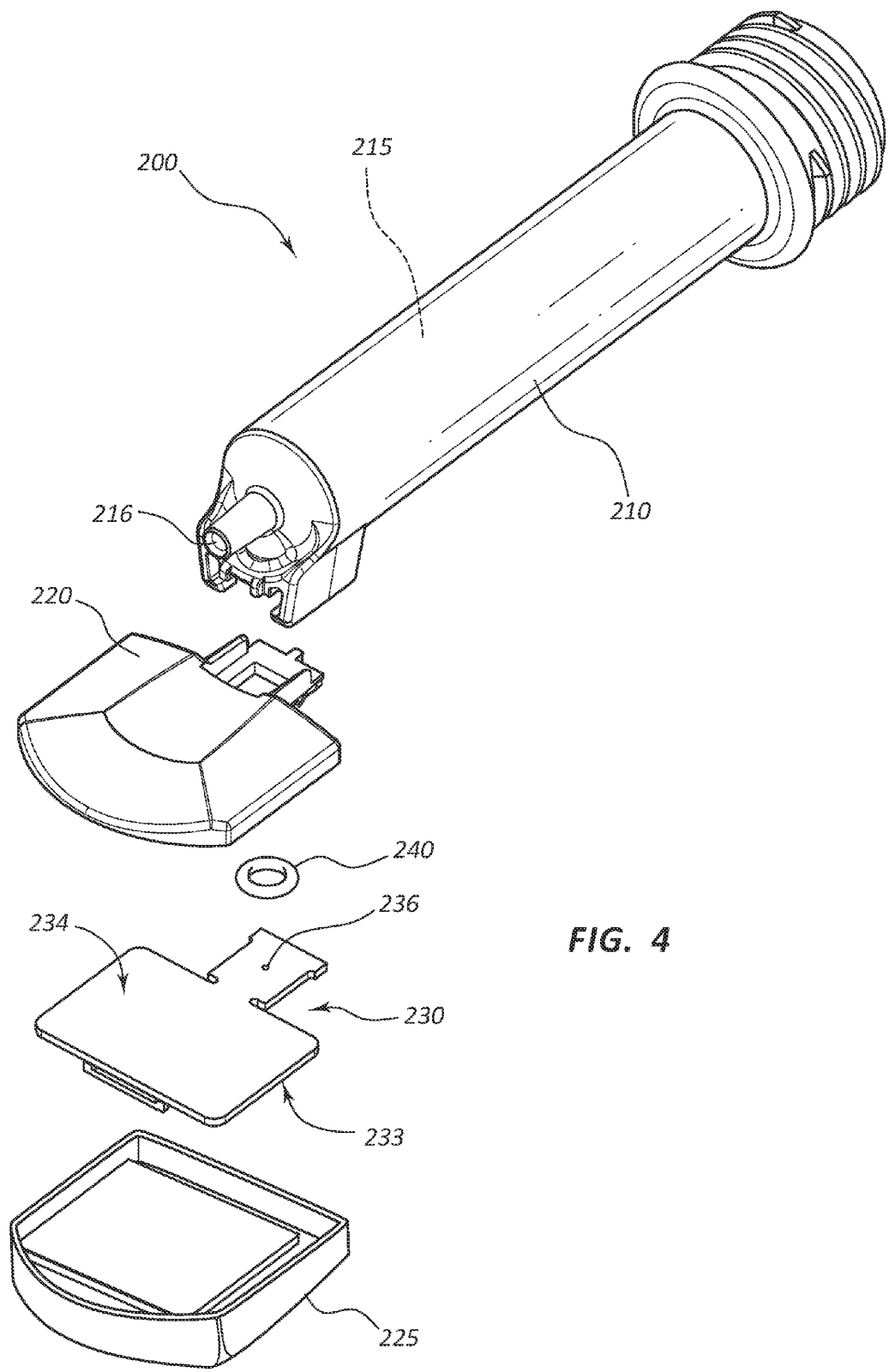
FIG. 4 is an exploded bottom view of the sensor assembly of FIG. 3.

FIG. 4 is an exploded bottom view of the sensor assembly 200 of FIG. 3. FIG. 4 illustrates the body portion 210, housing 220, outlet 216, display 225, sensor assembly 230, and o-ring 240. Furthermore, FIG. 4 illustrates a circuit board aperture 236 extending between the top 233 and bottom 234 surfaces of the circuit board 232. In the illustrated embodiment, the circuit board aperture 236 may be configured to provide fluid communication between the interior portion 215 and the sensor (235 of FIG. 3), in connection with the aperture (217 of FIG. 3). The o-ring 240 may be disposed to isolate the circuit board aperture 236 from fluid communication with the environment.

FIG. 5 is a side view of an inflation device 300 and housing 320. FIG. 5 further illustrates a handle 314, a body portion 310 having an interior portion 315, and a plunger 312. FIG. 5 further illustrates how displacement of the plunger 312 may change the pressure within the interior portion 315, and how the housing 320 may be positioned such that the display 325 is readily viewable by a practitioner using the inflation device 300.

FIG. 6 is an end view of the inflation device 300 and housing 320 of FIG. 5. FIG. 6 includes reference plane 7-7, showing the cross-sectional position of FIG. 7.

Figure 7:
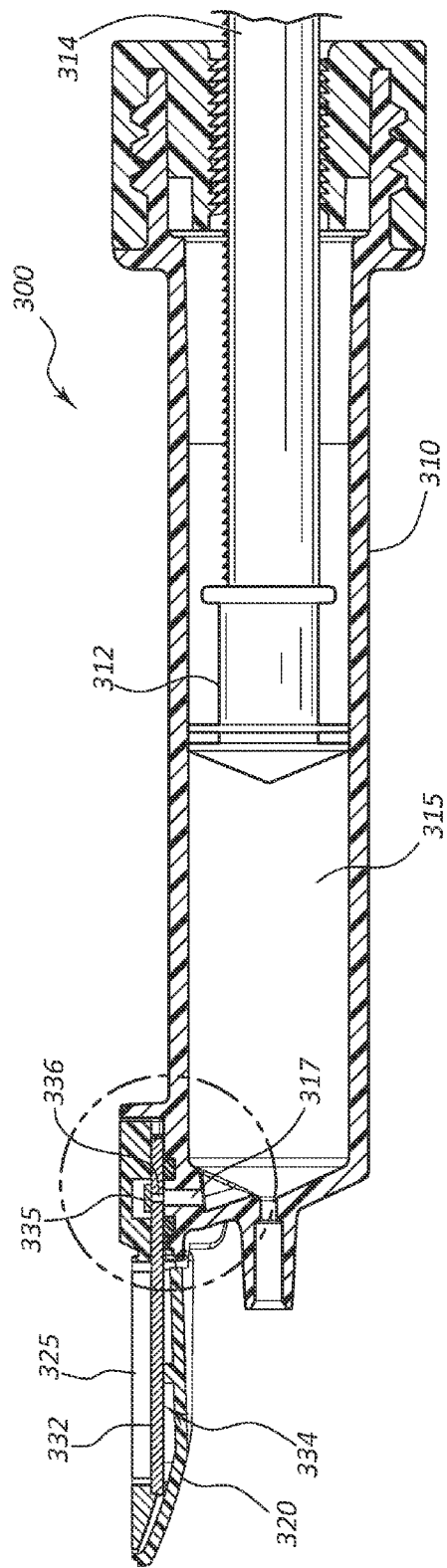
FIG. 7 is a cross-sectional view of the inflation device of FIG. 6, taken through plane 7-7.

Thus, FIG. 7 is a cross-sectional view of the inflation device 300 of FIG. 6, taken through plane 7-7. FIG. 7 illustrates the handle 314, the body portion 310 and interior portion 315, and the plunger 312.

Figure 7A:
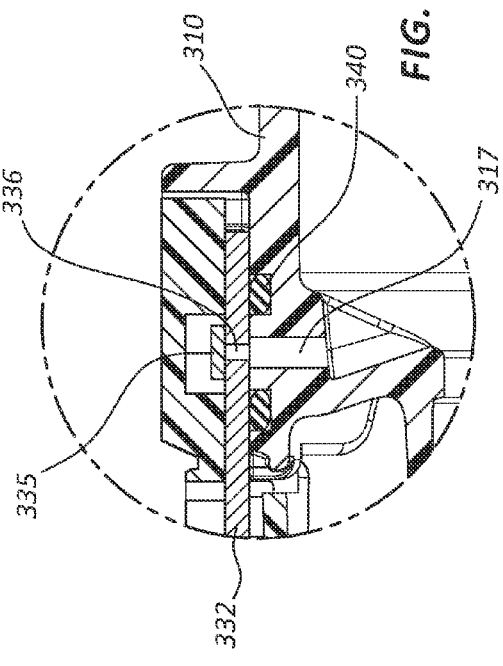
FIG. 7A is an enlarged view of the inflation device of FIG. 7, taken around line 7A-7A.

FIG. 7A is an enlarged view of the inflation device of FIG. 7, taken around line 7A-7A. FIG. 7A illustrates the relative positions of the housing 320, circuit board 332, and the display 325 when the component are assembled in this embodiment. FIG. 7A further illustrates how the aperture 317 and circuit board aperture 336 may be positioned to provide fluid communication from the interior portion 315 to the sensor 335. Again, in an embodiment wherein the sensor 335 is coupled to the bottom surface 334 of the circuit board 332, a circuit board aperture may be unnecessary.

Finally, FIG. 7A illustrates the position of the o-ring 340 with respect to the aperture 317, the circuit board aperture 336, the pressure sensor 335, and the housing 320. Again, the o-ring 340 may be configured to isolate the aperture 317, the circuit board aperture 336, and the pressure sensor 335 from the environment.

Without further elaboration, it is believed that one skilled in the art can use the preceding description to utilize the present disclosure to its fullest extent. The examples and embodiments disclosed herein are to be construed as merely illustrative and exemplary, not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. An inflation device comprising:
   a body member having an interior portion comprising a fluid chamber;
   a plunger disposed within the interior portion, the plunger configured to be axially displaceable with respect to the body member to change fluid pressure within the fluid chamber;
   a housing coupled to the body member, the housing configured to receive a sensor assembly;

a circuit board aperture extending between a first surface of a circuit board and a second surface of the circuit board, the circuit board aperture configured to allow fluid communication between the interior portion and the sensor assembly; and a seal member disposed such that a portion of the sensor assembly is in direct communication with the interior portion of the body and isolated from communication with an environment.

2. The inflation device of claim 1, wherein the seal member comprises an o-ring.

3. The inflation device of claim 2, wherein the o-ring is disposed around the circuit board aperture.

4. The inflation device of claim 1, wherein friction between the housing and the sensor assembly couples the sensor assembly to the housing.

5. The inflation device of claim 4, wherein the sensor assembly is coupled to the housing in a snap fit configuration.

6. The inflation device of claim 5, wherein the snap fit provides pressure on the seal member.

7. The inflation device of claim 1, wherein the sensor assembly comprises a circuit board and a sensor coupled directly to the circuit board.

8. The inflation device of claim 7, wherein the inflation device further comprises a display component coupled directly to the circuit board.

9. An inflation device comprising:
a body member having an interior portion comprising a fluid chamber;
a plunger disposed within the interior portion, the plunger configured to be axially displaceable with respect to the body member to change fluid pressure within the fluid chamber;
a housing coupled to the body member;
a sensor assembly coupled to the housing, the sensor assembly comprising a circuit board and a pressure sensor, the pressure sensor coupled such that the sensor directly abuts a circuit board surface; and
a seal member disposed such that a portion of the seal member directly abuts a circuit board surface.

10. The inflation device of claim 9, wherein the seal member is disposed such that a portion of the sensor assembly is in direct communication with the interior portion of the body and isolated from communication with an environment.

11. The inflation device of claim 10, wherein the sensor assembly is coupled to the housing by a snap fit connection.

12. The inflation device of claim 11, wherein the snap fit connection compresses the seal member.

13. The inflation device of claim 9, wherein the sensor is in direct communication with the interior portion.

14. A method of assembling an inflation device, comprising:
obtaining a body member comprising an interior portion;
coupling a sensor assembly to the body such that a sensor is in direct communication with the interior portion of the body member, the sensor disposed such that it directly abuts a circuit board surface; and
positioning a seal member in direct contact with a circuit board surface.

15. The method of claim 14, wherein coupling the sensor assembly comprises coupling the sensor assembly to the body member in snap fit configuration.

16. The method of claim 15, wherein positioning the seal member comprises positioning the seal member between the sensor and the body member.

17. The method of claim 16, wherein the seal member comprises an o-ring.

18. The method of claim 17, wherein the snap fit creates a compressive force on the o-ring.

* * * * *